United States Patent [19]

Tsutsumi et al.

[11] Patent Number: 5,353,544
[45] Date of Patent: Oct. 11, 1994

[54] FUMIGATION APPARATUS

[75] Inventors: Teruyuki Tsutsumi, Mihara; Tetsunori Sato; Akira Arita, all of Mihara, Japan

[73] Assignee: Teijin Chemicals Ltd., Tokyo, Japan

[21] Appl. No.: 990,237

[22] Filed: Dec. 14, 1992

[30] Foreign Application Priority Data

Dec. 16, 1991 [JP] Japan .................. 3-351853

[51] Int. Cl.$^5$ .......................... A01M 13/00
[52] U.S. Cl. ........................ 43/125; 43/124; 99/467; 99/468; 422/28; 422/108; 422/111; 422/125
[58] Field of Search .............. 422/28, 108, 305, 125, 422/110-111; 99/473, 467, 468; 43/124, 125

[56] References Cited

U.S. PATENT DOCUMENTS

| | | | |
|---|---|---|---|
| 4,989,363 | 2/1991 | Dorknemann | 43/124 |
| 4,998,377 | 3/1991 | Tsutsumi et al. | 426/320 X |
| 5,098,664 | 3/1992 | Schellhaas et al. | 422/108 |

*Primary Examiner*—Robert J. Warden
*Assistant Examiner*—Amaha L. Santiago
*Attorney, Agent, or Firm*—Sherman and Shalloway

[57] ABSTRACT

A fumigation apparatus is provided which uses mixed gas of hydrogen phosphide and methyl bromide, said mixed gas containing hydrogen phosphide at a high concentration, and which is free from the risk of ignition and safe. The apparatus, furthermore, is capable of fumigation that can completely kill noxious insects infesting green plants within a short time, exhibiting very little phytotoxicity on the plants and leaving extremely little residual fumigating agent after fumigation. Said apparatus is composed of (a) a system for purging air and hydrogen phosphide in a hydrogen phosphide path; (b) a system for hydrogen phosphide supply and transfer from a hydrogen phosphide bomb to a mixer through a humidifier; (c) a system for methyl bromide supply and transfer from a methyl bromide bomb to the mixer; and (d) a system for transferring the mixed gas from the mixer to a fumigation chamber.

7 Claims, 1 Drawing Sheet

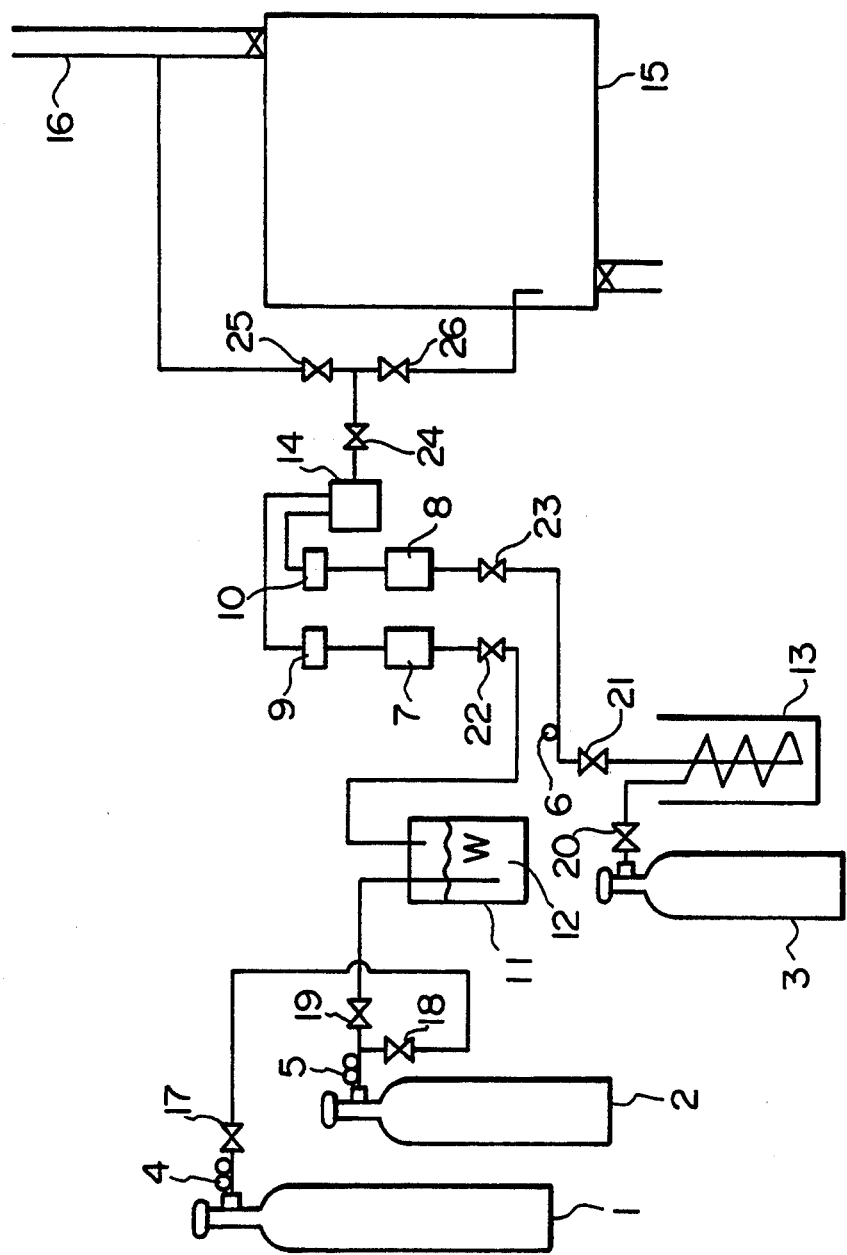

FUMIGATION APPARATUS

This invention relates to an apparatus for fumigation with a mixed gas of hydrogen phosphide and methyl bromide. More specifically, the invention relates to an apparatus for fumigation with a mixed gas of hydrogen phosphide and methyl bromide, which is capable of safely using hydrogen phosphide at a high concentration.

Hydrogen phosphide has been conventionally used for fumigation of warehouses of grains and green plants, silos, containers and barges. As well known, however, hydrogen phosphide is a highly dangerous gas which is liable to spontaneous ignition even at a low concentration (at a level of about 4 vol. %). For this reason, normally in fumigation with hydrogen phosphide, a method is adopted to generate hydrogen phosphide from aluminium phosphide tablets. However, an amount of hydrogen phosphide generated from aluminium phosphide tablets is largely affected by ambient humidity and temperature. Hence it is difficult to control the generation rate to constantly maintain a prescribed concentration. There is also a serious danger of ignition.

A method of charging hydrogen phosphide in a bomb and using it for fumigation is also known. Because of the earlier stated dangerously strong tendency of hydrogen phosphide to ignition, however, it is practiced to dilute high concentration hydrogen phosphide with an inert gas to a level of about 2 vol. % before charging it into a bomb, and to use so diluted gas for fumigation. Thus, the method is subject to a number of defects, i.e., an extra step of diluting high concentration hydrogen phosphide is required; a large number of bombs are necessary for fumigating a large size warehouse, for example, because such a low concentration hydrogen phosphide is used; at least 5 days' fumigation period is required because the hydrogen phosphide concentration within the warehouse cannot be raised; and, consequently, the method is not useful for fumigating anything for which freshness is a critical requirement.

In the recent years hydrogen phosphide is utilized also in the field of semiconductors. In this new field of use also, high concentration hydrogen phosphide is diluted with an inert gas to a concentration of about 20% or below before being charged in a bomb, and further diluted before use with an inert gas in a mixer provided with a flow meter, as a measure to prevent ignition. Therefore, it is neither practiced in this field to directly use high concentration hydrogen phosphide.

Accordingly, therefore, an object of the present invention is to provide an apparatus for fumigation which enables use of high concentration hydrogen phosphide free of risks of ignition and with safety, and which accomplishes complete kill of noxious insects infesting green plants within a short time, while keeping the phytotoxicity on the plants and remaining of the fumigating agent to the minimum levels.

We have noticed a fact that use of hydrogen phosphide and methyl bromide as a gaseous mixture can suppress phytotoxicity and enhance fumigation effect, and investigated on a fumigation method using such a gaseous mixture, with the view to accomplish the above object. In consequence, we came to know that favorable results can be obtained through that process, when hydrogen phosphide is used at concentrations higher than the conventionally used level.

Thus, according to the present invention an apparatus for fumigation which uses a mixed gas of hydrogen phosphide and methyl bromide is provided, which comprises:

(a) a system for purging air and hydrogen phosphide in a hydrogen phosphide path
(b) a system for hydrogen phosphide supply and transfer from a hydrogen phosphide bomb to a mixer, through a humidifier, preferably through a flow meter and a humidifier,
(c) a system for methyl bromide supply and transfer from methyl bromide bomb to the mixer, preferably through a flow meter, and
(d) a system for transferring the mixed gas from the mixer to a fumigation chamber.

BRIEF DESCRIPTION OF THE DRAWINGS

Hereinafter the present invention is explained, taking for example preferred embodiments thereof, referring to the attached drawing.

The drawing attached is a diagram illustrating an example of the apparatus of the present invention, in which 1 is a bomb of carbon dioxide gas, 2 is a bomb of hydrogen phosphide, 3 is a bomb of methyl bromide, 4 and 5 are pressure-controlling devices, 6 is a manometer, 7 and 8 are flow meters, 9 and 10 are integrating flow meters, 11 is a humidifier, 12 is water, 13 is a vaporizer, 14 is a mixer, 15 is a fumigation chamber, 16 is an exhaust cylinder, and 17, 18, 19, 20, 21, 22, 23, 24, 25 and 26 are valves.

The system (a), i.e., a system for purging air and hydrogen phosphide in the hydrogen phosphide path, functions to substitute the air in the hydrogen phosphide path with carbon dioxide gas. The system is composed of a bomb of carbon dioxide gas, pressure-controlling device 4, valves 17, 18 & 19, humidifier 11, valve 22, flow meter 7, integrating flow meter 9, mixer 14, valves 24 and 25, and an exhaust cylinder 16. Carbon dioxide gas may be replaced by another inert gas, such as nitrogen gas. It is also permissible to purge hydrogen phosphide in the hydrogen phosphide path by means of a vacuum pump. This purging of air in the hydrogen phosphide path is useful for prevention of hydrogen phosphide ignition.

The system (b), i.e., a system for hydrogen phosphide supply and transfer from the bomb of hydrogen phosphide to a mixer through a humidifier, preferably through a flow meter and a humidifier, is composed of a bomb of hydrogen phosphide 2, pressure-controlling device 5, valve 19, humidifier 11, valve 22, flow meter 7, integrating flow meter 9 and the mixer 14. The humidifier provided in this system functions very effectively for preventing ignition of hydrogen phosphide. The mechanism for its prevention of ignition is not yet fully clarified, but it is presumed that decomposition of the very minor amount of diphosphine in the hydrogen phosphide upon humidification contributes to the prevention of ignition. It is sufficient for the humidifier to only slightly humidify hydrogen phosphide. A humidifier of the type as indicated in the drawing, which causes hydrogen phosphide to pass through water (W), is simple and convenient. The humidifier 11 and flow meter 7 may be located by a reversed order from that in the drawing.

The system (c), i.e., a system for methyl bromide supply and transfer from a bomb of methyl bromide to the mixer, preferably through a flow meter, is composed of a bomb 3 of methyl bromide, valve 20, vaporizer 13, valve 21, manometer 6, valve 23, flow meter 8, integrating flow meter 10 and the mixer 14. Gasification of methyl bromide may be effected by a method of warming a methyl bromide can to vaporize its content, instead of using a vaporizer as indicated in the drawing. The flow meters used in this system and also in that for transferring hydrogen phosphide are not essential, which may be omitted or replaced by other measuring devices. The flow meters may be manually controlled or automatically controlled. Concurrent use of an integrating flow meter having an integrating function is recommended. More specifically, gas flowmeter, float-type, orifice type or mass flow meters, etc. may be used.

The system (d), i.e., a system for transferring the mixed gas from the mixer to a fumigation chamber, is composed of the mixer 14, valves 24 and 26, and a fumigation chamber 15. The form or model of the mixer is not critical, so long as it is provided with two separate paths for introducing hydrogen phosphide and methyl bromide, respectively, and it allows sufficient mixing of hydrogen phosphide and methyl bromide within a short time.

This fumigation apparatus is operable, for instance, by the following procedures.

(1) Purging of air in the hydrogen phosphide path with carbon dioxide gas:

The valve on the carbon dioxide bomb 1 is opened and jetting pressure is adjusted to a prescribed level (normally 0.5–10 kg/cm$^2$) with the pressure-controlling device 4. Then, first, valves 17, 18 and 19, and thereafter valves 22, 24 and 25 are opened to purge air in the hydrogen phosphide path with carbon dioxide gas. Upon completion of the purging valves 25, 19, 18 and 17 are closed.

(2) Introduction of methyl bromide gas into the exhaust route at a prescribed flow rate:

The valve on the methyl bromide bomb 3 and valve 20 are opened to introduce methyl bromide into the vaporizer 13. Then valve 21 is opened, and when the manometer 6 indicates a prescribed pressure level (normally 0.5–5 kg/cm$^2$), valves 23 and 24 are opened.

(3) Introduction of hydrogen phosphide gas into the exhaust route at a prescribed flow rate:

The valve on the hydrogen phosphide bomb is opened and jetting pressure is adjusted to a prescribed level (normally 0.5–10 kg/cm$^2$) with the pressure-controlling device 5. The valve 19 is opened, and then attainment of the prescribed mixing ratio of hydrogen phosphide and methyl bromide (methyl bromide: at least 10 vol. %, normally 30–70 vol. %) is confirmed. By controlling the ratio of methyl bromide to at least 10 vol. % here, ignition of hydrogen phosphide gas can be prevented.

(4) Supply of the mixed gas into the fumigation chamber (dosing):

The valve 26 is opened and a prescribed amount of the mixed gas is dosed to the fumigation chamber 15, while reading the amounts of the hydrogen phosphide gas and methyl bromide gas on the integrating flow meters 9 and 10.

(5) Termination of mixed gas supply (dosing):

When dosing of a prescribed amount of the mixed gas is terminated, the valve 26 is closed, that on the hydrogen phosphide bomb 2 and valve 19 are closed, then that on the methyl bromide bomb 3 and valve 20 are closed, and the valve 25 is opened.

The fumigation apparatus of the present invention is operable automatically or manually. Obviously, toxicity-neutralizing device for hydrogen phosphide and methyl bromide should be provided in the fumigation apparatus of the present invention. Any suitable system may be adopted for neutralize of the toxicity, such as adsorption, decomposition or combustion system.

The combination of the four systems (a), (b), (c) and (d) as above-described in the fumigation apparatus of the present invention allows safe use of high concentration hydrogen phosphide, free of fear of ignition. This achieves the excellent effect of reducing the cost of chemicals and drastic shortening of fumigation time.

What is claimed is:

1. Apparatus for fumigating the interior of a fumigation chamber with a mixed gas of hydrogen phosphide and methyl bromide, said apparatus comprising
   (a) a supply of pressurized hydrogen phosphide gas;
   (b) a supply of pressurized methyl bromide gas;
   (c) a supply of a pressurized inert gas;
   (d) a humidifier;
   (e) a conduit for transporting hydrogen phosphide gas from said supply (a) to said humidifier;
   (f) a mixer for mixing hydrogen phosphide gas from said supply (a) and methyl bromide gas from said supply (b) to form a mixed gas;
   (g) conduit means for transporting hydrogen phosphide gas from said humidifier to said mixer;
   (h) conduit means for transporting methyl bromide gas from said supply (b) to said mixer;
   (i) conduit means for transporting said mixed gas from said mixer to the fumigation chamber, and;
   (j) conduit means for transporting said inert gas from said supply (c) through said conduit means (e), said humidifier, said conduit means (g), said mixer and said conduit means (i) to the fumigation chamber to replace air in conduit means (e), (g) and (i) and in the humidifier and mixer with the inert gas.

2. The apparatus of claim 1 further comprising
   (k) means for monitoring flow of hydrogen phosphide gas through said conduit means (g).

3. The apparatus of claim 1 or claim 2 which further comprises
   (l) means for monitoring flow of methyl bromide gas through said conduit means (h).

4. The apparatus of claim 3 wherein said humidifier (d) comprises a container for water, an inlet for introducing hydrogen phosphide gas into the water present in said container, and an outlet for transporting the hydrogen phosphide gas which has passed through the water in said container to said conduit means (e).

5. The apparatus of claim 1 wherein said humidifier (d) comprises a container for water, an inlet for introducing hydrogen phosphide gas into the water present in said container, and an outlet for transporting the hydrogen phosphide gas which has passed through the water in said container to said conduit means (e).

6. The apparatus of claim 1 wherein the supply for pressurized methyl bromide comprises a source of liquid methyl bromide and vaporizing means for heating said liquid to vaporize the methyl bromide.

7. The apparatus of claim 1 wherein the supply for pressurized methyl bromide comprises a container with liquid methyl bromide contained therein, and means for heating said container to vaporize the methyl bromide contained therein.

* * * * *